United States Patent
Bessette et al.

(10) Patent No.: US 8,219,414 B2
(45) Date of Patent: Jul. 10, 2012

(54) METHOD OF APPRAISING A MAMMAL'S HEALTH

(75) Inventors: Russell W. Bessette, Orchard Park, NY (US); Michael J. Colson, East Amherst, NY (US)

(73) Assignee: Computer Task Group, Inc., Buffalo, NY (US)

( * ) Notice: Subject to any disclaimer, the term of this patent is extended or adjusted under 35 U.S.C. 154(b) by 893 days.

(21) Appl. No.: 11/903,846

(22) Filed: Sep. 25, 2007

(65) Prior Publication Data
US 2009/0024006 A1  Jan. 22, 2009

Related U.S. Application Data (60) Provisional application No. 60/959,670, filed on Jul. 16, 2007.

(51) Int. Cl.
G06Q 50/00    (2012.01)
G06Q 10/00    (2012.01)

(52) U.S. Cl. ............................................. 705/2; 705/3
(58) Field of Classification Search .................. 705/2
See application file for complete search history.

(56) References Cited

U.S. PATENT DOCUMENTS
5,594,637 A * 1/1997 Eisenberg et al. ............... 705/2
* cited by examiner

*Primary Examiner* — Robert Morgan
*Assistant Examiner* — Tran Nguyen
(74) *Attorney, Agent, or Firm* — Phillips Lytle LLP (57) ABSTRACT

An improved method of appraising a mammal's health includes the steps of: measuring the values of a plurality of factors indicative of different health parameters at a first time; normalizing the measured values of said factors at the first time; and arranging such normalized measured values at said first time in a first sequence; thereby to have said first sequence represent the mammal's health at the first time. The method may include the additional steps of: measuring the values of such plurality of factors at a second time; normalizing the measured values of such factors at the second time; arranging such normalized measured values in a second sequence; and comparing the second sequence with the first sequence or with a similar sequences from a plurality of similar animals recording the same primary afflicting condition.

17 Claims, 8 Drawing Sheets

Patient's PCIX Before Treatment 38 7.6 2.6 28 87 120 7

Patient's PCIX After Treatment 49 6.2 1.6 22 83 76 5

Normal PCIX 55 6 1.4 20 80 70 4

METHOD OF APPRAISING A MAMMAL'S HEALTH

CROSS-REFERENCE TO RELATED APPLICATIONS

The present application claims the benefit of the earlier filing date of provisional U.S. Pat. Appln. No. 60/959,670, filed Jul. 16, 2007.

TECHNICAL FIELD

The present invention provides an improved method of appraising a mammal's health at a particular point in time; of appraising the change in the mammal's health between two different points in time; of selecting, compensating and reviewing the performance of a health care provider as a function of such appraisal(s); and, in some cases, of providing feedback to the mammal on the status of its health.

BACKGROUND ART

As the cost of health care rises, many Americans seek a political solution. While some seek universal coverage through government-sponsored programs, others argue for more competition in managed care. But with health care costs approaching 17% of the GNP, and premiums rising by double digits annually, some people wonder if managed care is an experiment that has failed.

When it all began in 1930, managed care sought to harness costs through prevention and early diagnosis. (Tufts Managed Care Institute, "A Brief History of Managed Care", Managed Health care Directory Washington, D.C.; The AMCRA Foundation, CHAA/AMCRA, and 1995-1996; Bourdon, T., Passwater, K. and Priven, M., "An Introduction to Capitation and Health Care Provider Excess Insurance", www.casact.org/pubs/dpp/dpp97/97dpp097.pdf.)

Accomplishing this goal required information management. Even though it was paper-based, early efforts proved that linking patient symptoms to medical history and the results of past treatment not only improved quality, but also lowered cost. Yet despite their success, these plans faltered for nearly half a century, while fee-for-service medicine persisted. (Polzer, K, "Employee Health Plan Protections under ERISA", *Health Affairs*, 16(5):93-102; Enthoven, A. and Singer, S., "Perspective Markets and Collective Action in Regulating Managed Care", *Health Affairs*, 16(6):26-32; Wholey, D., Christianson, J., Engberg, J. and Byrce, C., "HMO Market Structure and Performance: 1985-1995", *Health Affairs*, 16(6):75-84.)

Finally in 1983, with costs boiling over, the Federal Government took drastic action. Empowered by new legislation, Medicare began to pay hospitals only a portion of their customary fees based on a rate determined by one of 467 diagnosis-related groups (DRG). Shortly thereafter, private insurance released a wave of similar plans. But even with price control, which stabilized the market for a brief period, costs soon rose. (Bailit, M., "Perspective: A Purchaser's View of Health Care Market Trends", *Health Affairs*, 16(6):85-88; Hellinger, F., "Any Willing Provider and Freedom of Choice Laws: An Economic Assessment", *Health Affairs* 14(4):297-302; Herzlinger, R., "Market-Driven Health care: Who Wins, Who Loses in the Transformation of America's Largest Service Industry", Perseus Books, Harper Collins Publishers, NY (1997).)

In an effort to regain control, managed care restructured itself and introduced capitation, preferred provider networks and pay-for-performance concepts. Under these new paradigms, hospitals merged into vertically-integrated giants that promised greater efficiency and lower cost through economies of scale. (Goldsmith, J., "Hospitals and Physicians: Not a Pretty Picture", *Health Affairs*, 26(1):72-75; Berenson, R., Ginsburg, P. and May, J., "Hospital-Physician Relations Cooperation, or Separation?", *Health Affairs*, 26(1):31-43; Goldsmith, J. and Kaufman, N., "Between a Rock and a Hard Place: Physician Markets Create New Strategic Problems for Hospitals", COR Health care Market Strategist (November 2004).)

Unfortunately, medical information systems lagged behind these initiatives. Despite the cutting-edge use of computers in radiology and surgery, payers used computers primarily for billing and tracking procedures. Even today, considerable patient data remains locked on handwritten notes scattered across physician offices and clinics. As a result, other than the thirty-five HEDIS-mandated effectiveness-of-care measures, such as childhood immunization, hypertension control, cholesterol and beta-blockers after heart attack, colon and breast cancer screening, payers and patients primarily judge quality by price.

Generally in a free market system, competition improves products and lowers price. But in a complex service industry, like health care, prices may not reflect quality. Consumers require outcome data along with price. Absent this information, choice is governed by commercials, ads and anecdotes.

Whenever a patient faces a major medical decision, family and friends generally ask three questions: Who's your doctor? What did the doctor say? Should you get a second opinion? Under-pinning each question is the need for answers based in outcome data. Matching patients with the right doctor requires knowledge on how patients with similar conditions have responded to treatment from different providers. In addition, ethnic, family, and social needs are a concern. Collectively, this determines value.

To provide these answers, an information system must sort through electronic medical records that contain objective laboratory and clinical data, along with disability measurements, and treatments, and then correlate these to cost and outcome. Since this information is dynamic and voluminous, it must be organized and merged with existing IT systems that track codes for payment in order to draw outcome-based conclusions. Finally these conclusions must be displayed in formats that facilitate patient understanding and choice.

In the end, the question is not whether managed care failed, but rather, was information managed properly? In health care, there are three stakeholders: (a) patients seeking services at a reasonable cost; (b) payers seeking profitable risk encapsulation, and (c) providers seeking fair compensation for quality care. Each stakeholder has a unique viewpoint.

Patients are chiefly concerned with health conditions; a condition being defined as a set of symptoms and disabilities that require medical treatment over time. In most cases, with proper care, conditions improve; in others, despite superior treatment, the disease advances. However, in all cases, patients measure value by both objective and subjective means. Generally, they focus on pain relief and disability reduction. Next, they react to how that care was delivered. If medical informatics is to assist patients in selecting value, then it should display treatment results from various providers within a format that considers similar stages of disease, and co-existing problems unique to that patient.

Since value is outcome over cost, certain questions set the bench mark. Was the outcome worth the cost? Were the end results, and the improvement, worth the time and expense? During the treatment period, were the services rendered in clean comfortable facilities, by providers working together, in a manner that respected cultural differences? Such assessments consider both the science and psychology of medicine. Together they produce the final score, subjectively perceived as quality.

As outlined in Porter, M. and Teisberg, E., "Redefining Health Care: Creating Value-Based Competition on Results", Harvard Business School Publishing, Boston Mass. (2006), these value-based outcomes should be the criteria by which providers are judged and the basis for patient-centric competition in health care.

Payers in health care are concerned with financial risk management and encapsulation of financial risk. They provide patients, employers, and the government with financial security for subscribed periods of time. The security they provide is intended to mitigate the financial consequences of disease or injury. Generally, this is achieved through financial risk management, which, to be profitable, requires accurate information on likely outcomes for specific medical conditions. Ideally, it should be achieved through ontology-driven principles that analyze clinical and laboratory data, as well as pain and disabilities before and after treatment. The current system of pooling patients under a primary ICD-9 diagnostic code and then inferring quality by the least number of CPT procedures used, disregards patient complexity, provider skills, and patient outcome.

To form value-based conclusions, patients must be grouped according to similar if not identical medical conditions. Grouping patients based on a single diagnostic (ICD-9) code will not account for complexity caused by other health cofactors such as age, obesity, renal disease, diabetes, hypertension, heart failure, or mental challenges, to name but a few. Therefore, even though patients come to providers concerned over a single chief complaint, their baseline measurement must include values that represent not only the primary disability but also all relevant health co-factors.

Next, these measurements should be standardized (i.e., normalized) and ranked according to how they influence treatment of the primary condition. Taken together, these values produce a composite number that depicts the primary disability but also relates other health cofactors that might influence outcome. We refer to this as a Patient Complexity Index ("PCIX").

Following treatment, the change in that PCIX reflects the response to therapy. Though the amount of improvement may differ in patients, by measuring it, this system provides payers with data to evaluate disease severity and complexity, along with a patient's response to treatment. Furthermore, when this scale is coupled with cost, it permits comparison of providers by efficiency and cost.

For example, two patients with identical knee injuries might demonstrate the same restricted joint flexion, but because one of them has severe complicating health cofactors, they differ markedly from each other. Grouping these patients together under a single primary diagnostic code and expecting similar outcomes is unrealistic and prevents analysis of why their results might differ. Since current information systems are blind to the spectrum of health in any given patient, as a result they are grouped by chief complaint and their treatment is judged by the number of employed procedures and cost. This method also assumes that all providers can achieve identical results for similar problems. With no mechanism to identify best practice, payers can only achieve cost-saving by driving procedure prices lower, or delaying care.

Without multi-faceted outcome data, most providers and patients will consider pain relief as the single most-important indicator of effectiveness of treatment. Unfortunately, this is subjective and possibly temporary. Furthermore with cancer patients, it fails to answer the question as to whether the condition has been improved, or merely placated.

Since clinical measurements and laboratory data comprise a patient's unique health index, the tests which compose it should be selected and weighted in importance by national guidelines for each specific diseases and the relationship of cofactors to it. Furthermore, the system should be flexible and accommodate new diagnostic tests or treatments, as well as new understandings of co-conditions to a primary disease.

Providers employ the scientific method in nearly everything they do, except when it comes to having outsiders evaluate their work. Even if anxiety could be eliminated from the review process, there is still the need to grade physician skill and not blame disease severity and poor patient health for treatment failure. Without the ability to analyze and compare outcomes based on complete electronic medical records, failure is relegated to subjective opinions that are difficult to refute. Besides being unfair to patients, it impedes best quality practice and physician self-improvement.

Within an amorphous metric system, it's difficult to set goals and hold providers accountable. Plus, if providers have inadequate skills and enter a capitation agreement that includes patients with high complexity, they are likely to dissatisfy everyone.

On the other hand complete medical informatics allows providers to be selected and paid according to outcome data for patients with similar complexity. In this patient-centric manner, a serious impediment to capitation is removed, and the tendency to spiral sicker patients down an endless referral pattern is minimized. By recognizing the influence of relevant health co-factors and scaling payment to it, patients can be directed to integrated practice units with track records for success in comparable complexity. In such an information system, superior providers are identified and their achievements rewarded with more patient referrals.

DISCLOSURE OF THE INVENTION

With parenthetical reference to the corresponding parts, portions or surfaces of the disclosed embodiment, merely for purposes of illustration and not by way of limitation, the present invention broadly provides an improved method of appraising a mammal's health.

The improved method broadly includes the steps of: measuring the values of a plurality of factors indicative of different health parameters at a first time; providing such first-time measured values to a computer; causing the computer to normalize such first-time measured values; and causing the computer to arrange such normalized first-time measured values in a first sequence; thereby to have the first sequence represent the mammal's health at the first time.

This method may include the additional step(s) of: storing the first sequence and/or recording a first condition adversely affecting the mammal at the first time and/or recording the first condition; and/or selecting the health parameters affecting the first condition, measuring the values of a plurality of factors affecting such selected health parameters, and normalizing the measured values of such selected factors; and/or storing the health parameters affecting the first condition. Each of the measured values may be normalized about a number selected to represent a normal value (e.g., 100%) of the associated factor.

The improved method may further include the additional step of: displaying such sequence. The first sequence may be displayed by first listing the condition adversely affecting the mammal, and by then listing the normalized measured values of the selected factors affecting the condition in descending order of influence and importance. The sequence may be displayed linearly or graphically.

The improved method may further include the additional steps of: measuring the values of the plurality of factors indicative of the different health parameters at a second time, providing or supplying such second-time measured values to the computer; causing the computer to normalize such second-time measured values, and causing the computer to arrange such normalized second-time measured values in a second sequence, thereby to have the second sequence represent the mammal's health at the second time.

The improved method may further include the additional step(s) of: storing the second sequence and/or comparing the second sequence to the first sequence; thereby to discern changes in the health of the mammal between the first and second times.

The improved method may further include the additional step of: comparing at least one of the sequences from the mammal with similar sequences from a plurality of similar mammals recording the same primary afflicting condition.

The mammal may be treated by a health care provider for the condition. The improved method may further include the additional step(s) of: selecting the health care provider as a function of the comparison, compensating the health care provider as a function of the comparison, and/or reviewing the performance of the health care provider as a function of the comparison.

Accordingly, the general object of the invention is to provide an improved method of appraising a mammal's health.

Another object is to provide a criteria to assist in the selection of a health care provider.

Another object is to provide a criteria for compensating a health care provider.

Still another object is to provide a criteria for reviewing the performance of a health care provider.

These and other objects and advantages will become apparent from the foregoing and ongoing specification, the drawings and the appended claims.

DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Co-factors, such as diabetes, hypertension, renal failure, congestive heart failure, obesity, etc. profoundly impact treatment results. Besides producing poor outcomes for ostensibly simple medical procedures in a patient of normal health, they unfairly stigmatize patients who are afflicted with them. Such patients may have care denied or delayed. Not only does this penalize the patient, but it also perpetuates a poor view of payers.

To address these problems, we propose the use of a Patient Complexity Index (PCIX) composed of key clinical and laboratory values for various relevant functional tests associated with the primary medical condition and potential co-factors that could inhibit treatment or healing. For each patient, the PCIX can be displayed graphically on a radar chart or as a polar array, so that the key value associated with the primary medical condition occupies the 12 o'clock position on the chart, and the values of the co-factors relevant to that particular primary medical condition are arranged clockwise in descending order of impact on the primary condition. Before a patient's absolute laboratory and clinical values are plotted, their raw values are adjusted so that a normal value for each test would scale to one-hundred percent. These normalized values would have equal radii in the radar chart. Thus, when a patient with normal values is plotted, his graph would appear substantially as a circle or an O.

However, when abnormal values are adjusted by the same factor and plotted, they produce a non-circular shape, such as a deformed ellipse or a polygon. The greater the deviation from normal, the more the unit-radius circle is deformed. As a result, patients and payers can both quickly visualize disease complexity and the influence of co-factors.

Figure 1:
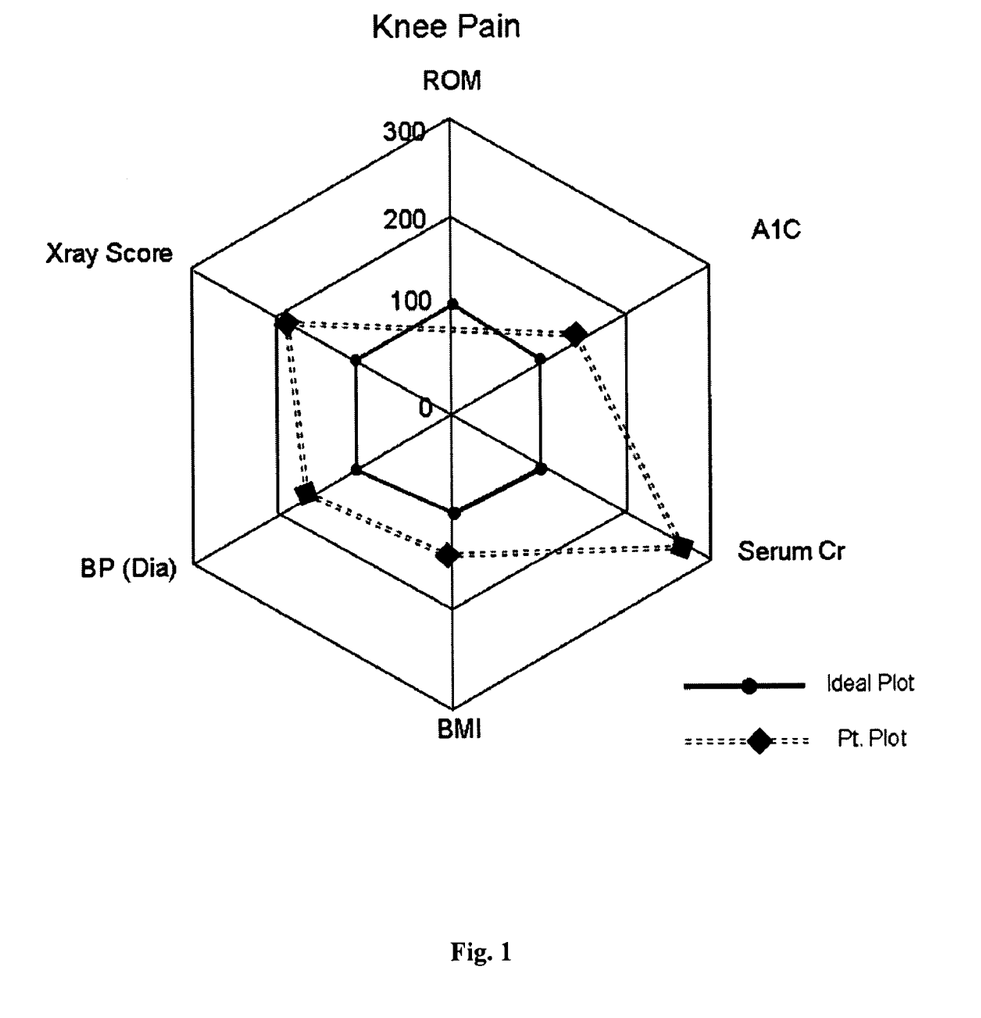
FIG. 1 is a schematic radar chart of a PCIX for a patient with primary knee pain, this view showing the patient's normalized individual test results as compared with those of an ideal patient.

Consider, for example, a patient (AB) with knee pain and moderate limitation of flexion by some twenty degrees. Absent the knowledge of his particular co-factors, the limited data of the primary affliction suggests a mild problem. However, when the patient's diabetes (A1c), kidney disease (Serum Cr), hypertension (BP) and obesity (BMI) are plotted, as in FIG. 1, it is readily apparent this case is more complicated. In all likelihood, the outcome might prove costly. Encapsulating this risk before treatment provides both payers and providers with a guide as to whether a specialized or experienced practice unit might be expected to achieve a better result.

When the normalized values for all co-factors are grouped together as a single numeric or word, a unique PCIX is produced for each patient. With individual values located in standard positions, like digits within a telephone number that identify area code, prefix, and line number, the PCIX now permits automated comparison of similar patients, treatment outcomes and costs, within a database.

With the value for the primary disability located at the first group position, the remaining co-factor measurements can be ranked linearly from left to right according to their impact on the primary afflicting condition. The location of each co-factor within the PCIX for a given primary affliction ultimately depends on recommendations of national standards and boards. But the end result would be a patient-specific number that positions a patient along a severity scale for risk and complications. Additionally, by coupling this PCIX to existing and already employed DRG and ICD-9 codes, this value-based outcome measurement can be phased into present information systems. As more patient specific laboratory data becomes available, the database can be upgraded and expanded.

Figure 2:
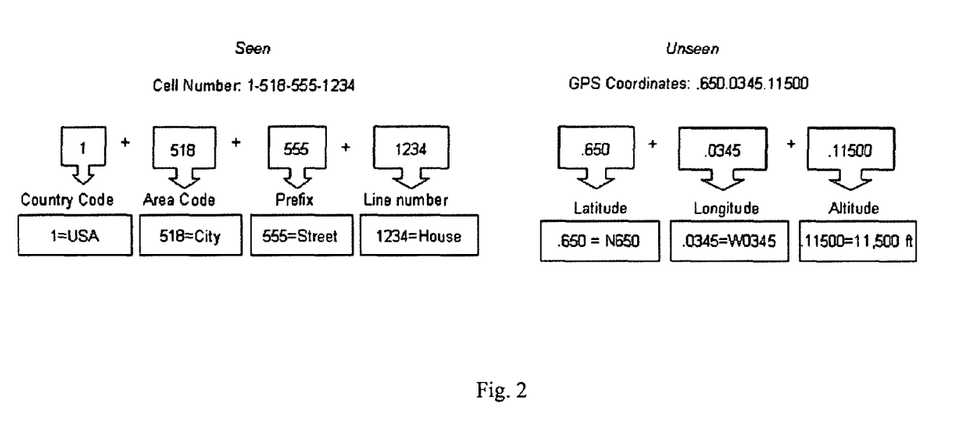
FIG. 2 is a schematic demonstrative likening a patient's sequence to a cell phone number or a GPS coordinate system.

Continuing the analogy for comparing PCIX to a telephone number, FIG. 2 illustrates how location of digits within a phone number might convey specific information. Though some numbers, like area code and cell number, are readily known to the customer, other digits, such as GPS coordinates, altitude and other identification numeric are unseen, but are available for data extraction.

Figure 3:
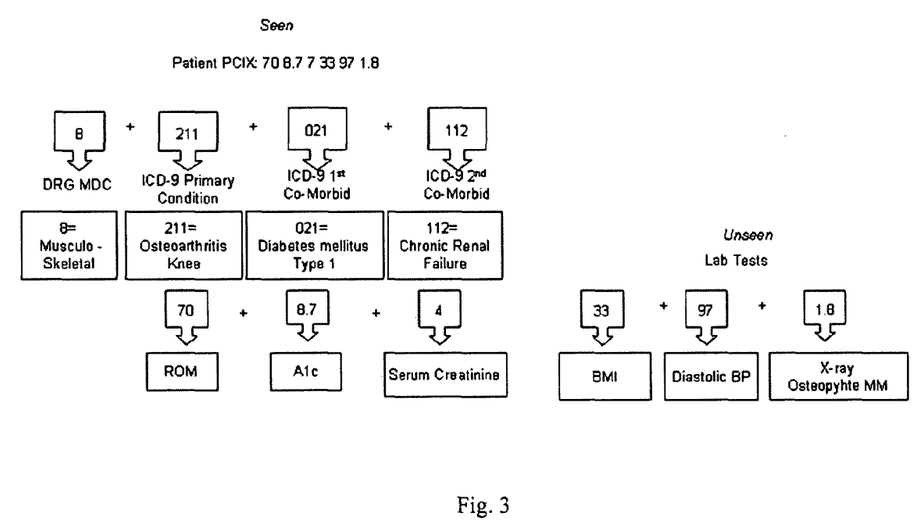
FIG. 3 is a further demonstrative of a patient's PCIX.

As shown in FIG. 3, specific clinical and laboratory measurements can be linked to existing known data, such as DRG codes and ICD-9 codes. Other critical measurements can be attached to this numeric. Matching the clinical and lab data for patient AB to existing DRG and ICD-9 data produces the composite word shown in FIG. 3.

Figure 4:
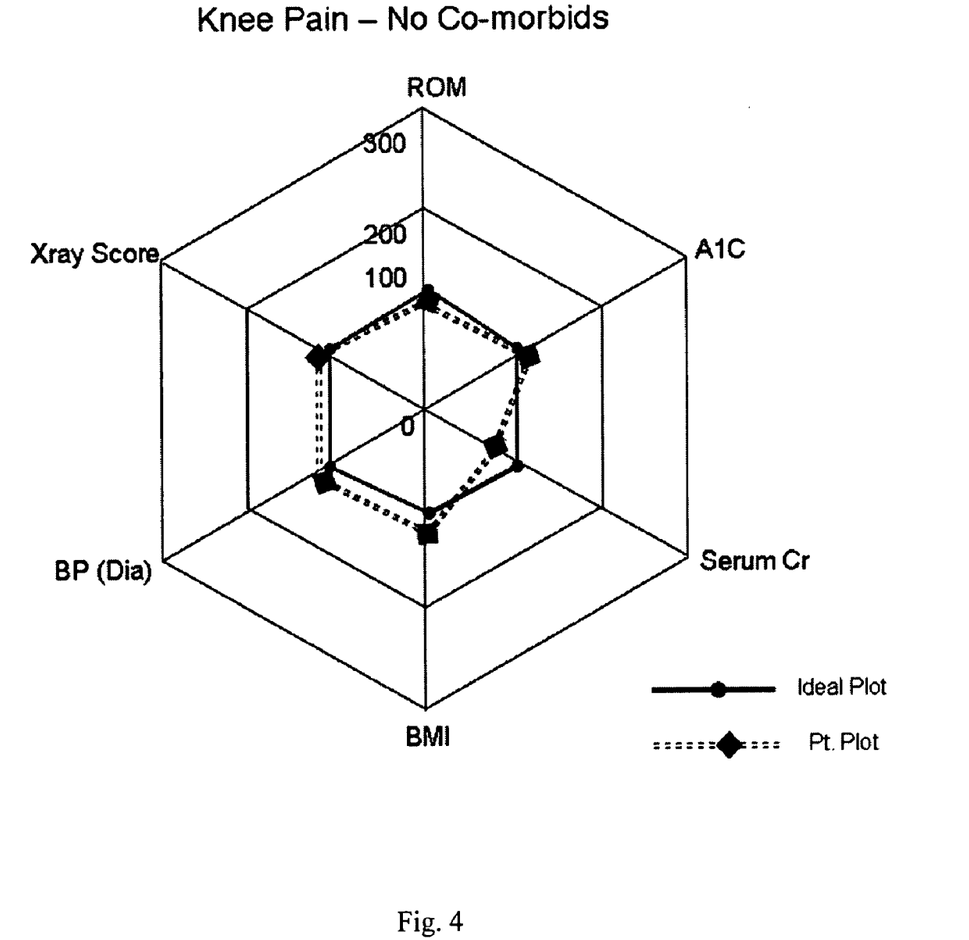
FIG. 4 is a schematic radar chart of a PCIX for a patient with knee pain, but with significantly-abnormal no co-factors.

FIG. 4 depicts another patient with the same degree of limited knee flexion, but only minor co-factors. The slight variation from the normal circle readily depicts a healthy patient suffering only from knee arthritis.

Heart attack is another medical condition consuming major portions of a medical budget. Frequently, it occurs in individuals afflicted with several co-factors. The treatment and rehabilitation of heart attack patients depends on controlling these co-factors. Presenting their relationship to patients in a unified plot might help them understand their progress, as well as motivate compliance with rehabilitation therapy.

Figure 5:
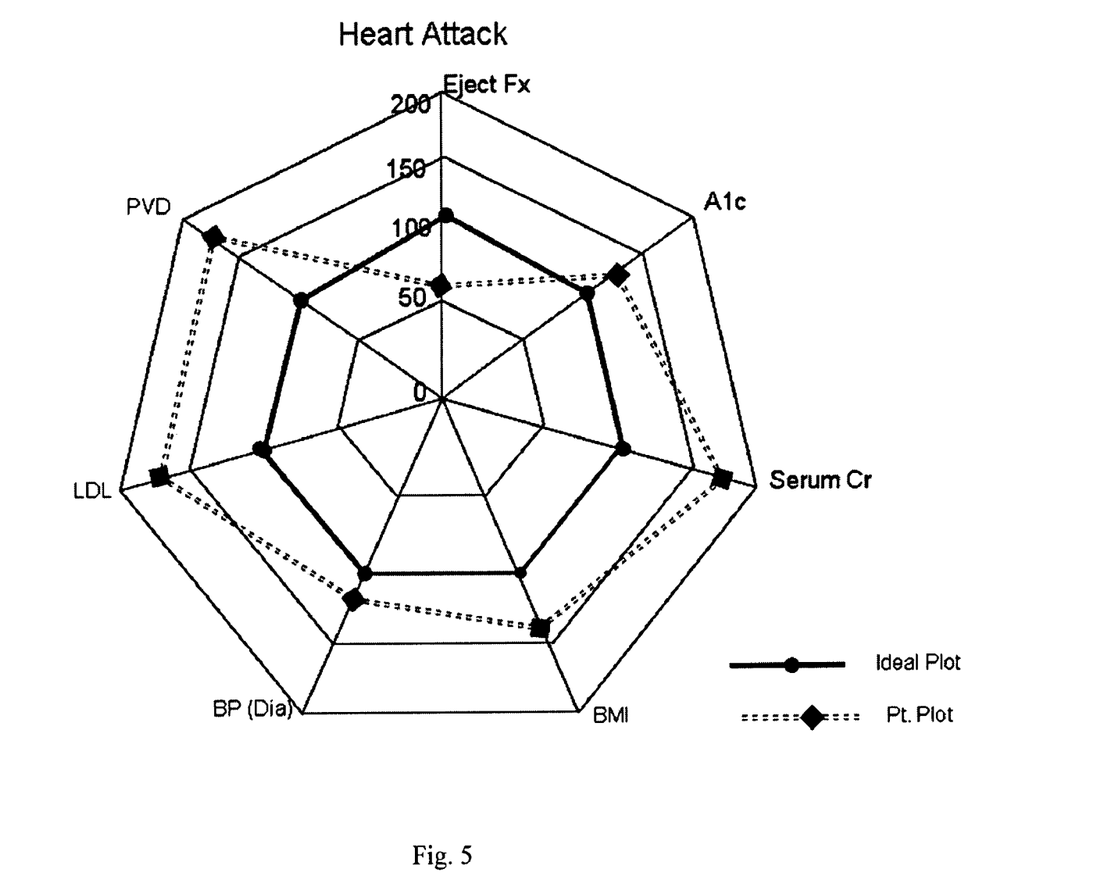
FIG. 5 is a schematic radar chart of a PCIX for a patient who has had a heart attack, showing the patient's profile as a departure from the expected norm.

FIG. 5 displays a typical heart attack patient directly after hospital admission. The patient's primary disability is reduced cardiac ejection. However obesity, hyperlipedema, diabetes, and hypertension all influence the outcome. Like the preceding example, the deformed graph pattern and its deviation from normal is readily apparent.

Figure 6:
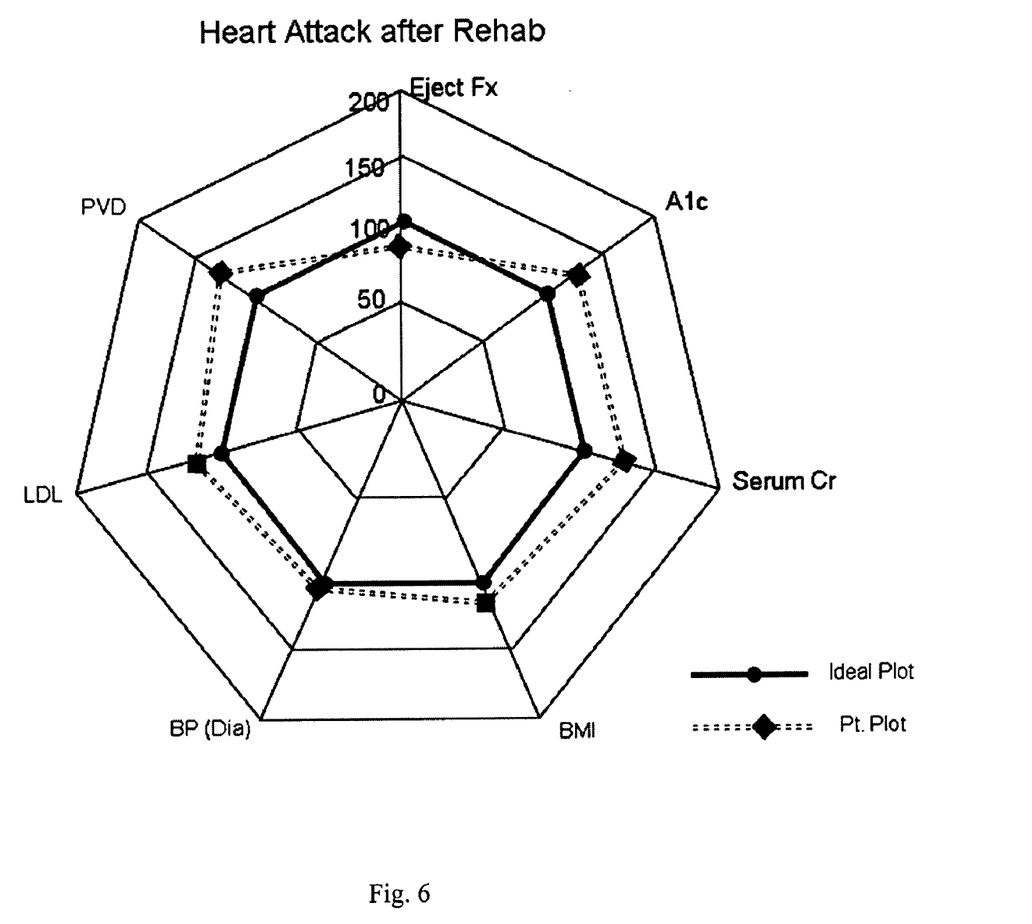
FIG. 6 is a schematic radar chart of a PCIX for the heart attack patient shown in FIG. 5, after some period of rehabilitation.

Following treatment that included coronary artery stents, a program of physical reconditioning, and medical treatment with dietary changes reveals four months later the graph shown in FIG. 6.

The components of the PHI which created this patient's unique identifier included the following measures: cardiac ejection fraction as the primary measure of this disability, glycosylated hemoglobin (A1c) for diabetes, serum creatinine (Serum Cr) for kidney function, body mass index (BMI) for obesity, diastolic blood pressure (BP) for hypertension, LDL for low density lipoproteins (bad cholesterol), and PVD for clinical presence of peripheral vascular disease.

Figure 7:
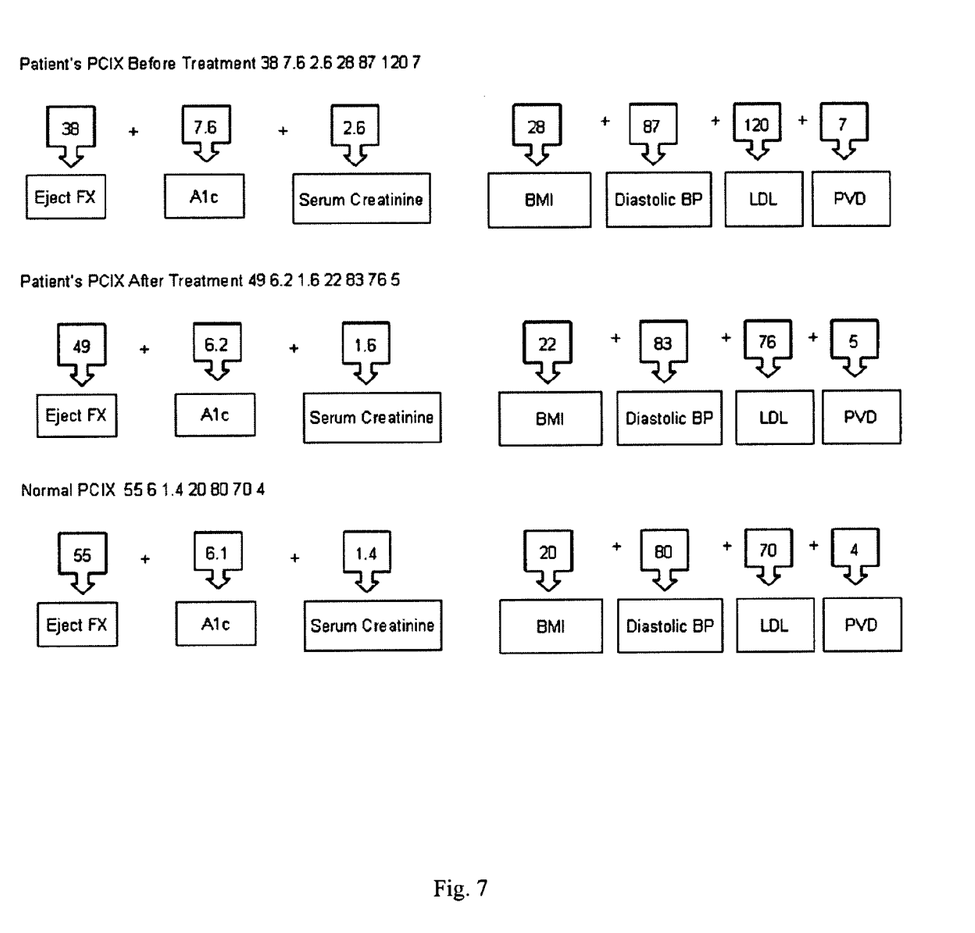
FIG. 7 is a schematic demonstrative showing the comparison of a patient's PCIX before and after treatment, and compared to a normal PCIX.

Displaying these values and comparing them before and after treatment to normal reflects the improvement, as shown in FIG. 7.

By grouping these values in standard positions, comparisons can be made based upon treatment specifics, cost, duration and percent improvement. As payers group insured clients according to condition severity and their unique PCIX, they will soon accumulate outcome data identifying preferred treatments and providers. Since value is outcome over cost for selected periods of time, payers can now construct value-based outcome curves for each similar medical condition. By separating patients into groups representing similar degrees of complexity, pay-for-performance curves can now be constructed that rewards providers for achieving best practice outcomes.

Figure 8:
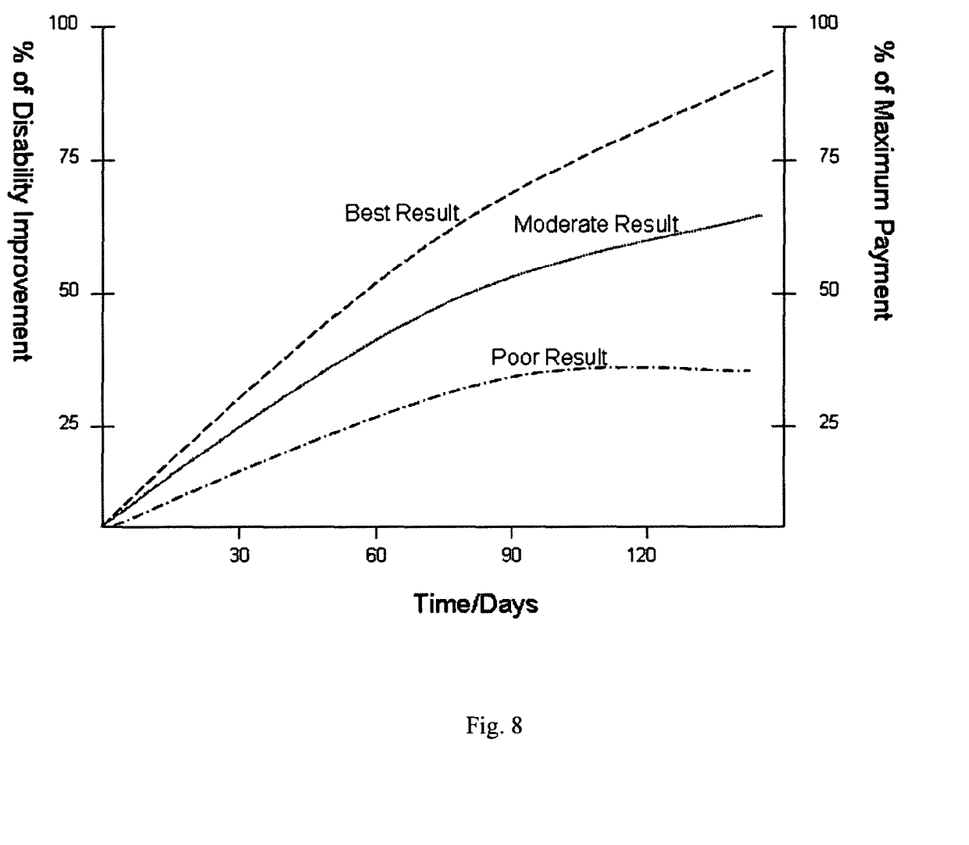
FIG. 8 is a plot of percentage of disability improvement (left ordinate) and percentage of maximum payment (right ordinate) vs. time (abscissa).

FIG. 8 displays three example curves that might result according to percent improvement in disability for patient pools with similar PCIX. Providers, whose results fall on the best practice curve, would expect compensation at the 100% level, and inclusion in a network of preferred providers. On the other hand, providers whose results fell on less desirable curves might expect to find themselves excluded from future capitation agreements, or be given opportunities to re-evaluate their treatment methods.

Since this new paradigm builds upon existing information systems employed within many payer organizations, it can introduce value-based outcome methods and PCIX through a series of pilot programs for select medical conditions. By coupling laboratory data from the EMR to existing ICD-9 codes already used for billing, payers can evaluate new risk encapsulation programs that link pay-for-performance to more objective outcome data.

Therefore, while the presently-preferred form of the improved method has been shown and described, and several modifications thereof discussed, persons skilled in this art will readily appreciate that various additional changes and modifications may be made without departing from the spirit of the invention, as defined and differentiated by the following claims.

What is claimed is:

1. The method of appraising a mammal's health, comprising the steps of:
measuring the values of a plurality of factors indicative of different health parameters at a first time;
supplying such first-time measured values to a computer;
causing said computer to normalize such first-time measured values about numbers selected to represent normal values of said factors; and
causing said computer to arrange such normalized first-time measured values in a first sequence;
thereby to have said first sequence represent the mammal's health at said first time.

2. The method as set forth in claim 1, and further comprising the additional step of:
recording a first condition adversely affecting said mammal at said first time.

3. The method as set forth in claim 2, and further comprising the additional steps of:
selecting the health parameters affecting said first condition;
measuring the values of a plurality of factors affecting such selected health parameters; and
causing said computer to normalize the measured values of such selected factors.

4. The method as set forth in claim 3, and further comprising the additional step of:
displaying such sequence.

5. The method as set forth in claim 4 wherein said first sequence is displayed by first listing the condition adversely affecting said mammal, and by then listing the normalized measured values of said selected factors.

6. The method as set forth in claim 5 wherein said sequence is displayed linearly.

7. The method as set forth in claim 5 wherein said sequence is displayed graphically.

8. The method as set forth in claim 3, and further comprising the additional step of:
storing said health parameters affecting said first condition.

9. The method as set forth in claim 2, and further comprising the additional step of:
comparing at least one of said sequences from said mammal with similar sequences from a plurality of similar mammals recording said condition.

10. The method as set forth in claim 9 wherein said mammal is to be treated by a health care provider for said condition.

11. The method as set forth in claim 10, and further comprising the additional step of:
selecting said health care provider as a function of said comparison.

12. The method as set forth in claim 10, and further comprising the additional step of:
compensating said health care provider as a function of said comparison.

13. The method as set forth in claim 10, and further comprising the additional step of:
reviewing the performance of said health care provider as a function of said comparison.

14. The method as set forth in claim 1, and further comprising the additional steps of:
measuring the values of said plurality of factors indicative of said different health parameters at a second time;
providing such second-time measured values to a said computer;
causing said computer to normalize such second-time measured values about numbers selected to represent normal values of said factors; and
causing said computer to arrange such second-time normalized measured values in a second sequence;
thereby to have said second sequence represent the mammal's health at said second time.

15. The method as set forth in claim 14, and further comprising the additional step of:
storing said second sequence.

16. The method as set forth in claim 14, and further comprising the additional step of:
comparing said second sequence to said first sequence to discern changes in the health of said mammal between said first and second times.

17. The method as set forth in claim 1, and further comprising the additional step of:
storing said first sequence.

* * * * *